United States Patent
Zitzke et al.

(10) Patent No.: US 10,064,434 B2
(45) Date of Patent: Sep. 4, 2018

(54) ELECTRONIC SMOKING DEVICE WITH HEATER POWER CONTROL

(71) Applicant: FONTEM HOLDINGS 1 B.V., Amsterdam (NL)

(72) Inventors: Roland Zitzke, Bienenbüttel (DE); Vaclav Borkovec, Hamburg (DE)

(73) Assignee: FONTEM HOLDINGS I B.V., Amsterdam (NL)

( * ) Notice: Subject to any disclaimer, the term of this patent is extended or adjusted under 35 U.S.C. 154(b) by 3 days.

(21) Appl. No.: 15/086,977

(22) Filed: Mar. 31, 2016

(65) Prior Publication Data

US 2016/0213066 A1 Jul. 28, 2016

Related U.S. Application Data

(63) Continuation of application No. PCT/EP2014/002646, filed on Sep. 29, 2014.

(30) Foreign Application Priority Data

Oct. 2, 2013 (EP) .................................... 13004749

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
None
See application file for complete search history.

(56) References Cited

U.S. PATENT DOCUMENTS 5,388,594 A * 2/1995 Counts .................. A24F 47/008
128/202.21
5,505,214 A * 4/1996 Collins ................. A24F 47/008
128/202.21
(Continued)

FOREIGN PATENT DOCUMENTS

CN 104026742 A 9/2014
EP 2443946 A1 4/2012
(Continued)

OTHER PUBLICATIONS

European Patent Office, European Search Report issued in EP Patent Application No. 13004749.1 (dated Nov. 9, 2014).
(Continued)

*Primary Examiner* — Tho D Ta
(74) *Attorney, Agent, or Firm* — Perkins Coie LLP; Kenneth H. Ohriner

(57) ABSTRACT

An electronic smoking device comprises a housing accommodating a battery (10) as an electric power source powering an electrically heatable atomizer comprising an electric heater (22) and adapted to atomize a liquid supplied from a reservoir to provide an aerosol exiting from the atomizer. The heater (22) of the atomizer is controlled by means of control electronics (14). A puff detector (18) indicates an aerosol inhaling puff to the control electronics (14). The control electronics (14) operates, for a puff, the heater (22) of the atomizer with a pre-determined level of electric power. Preferably, the electronic smoking device comprises a voltage sensor (34) measuring the battery voltage, wherein the control electronics (14) distributes the pre-determined level of electric power, for a puff, by pulse width modulation, based on the battery voltage measured by the voltage sensor (34).

19 Claims, 2 Drawing Sheets

Figure 3:
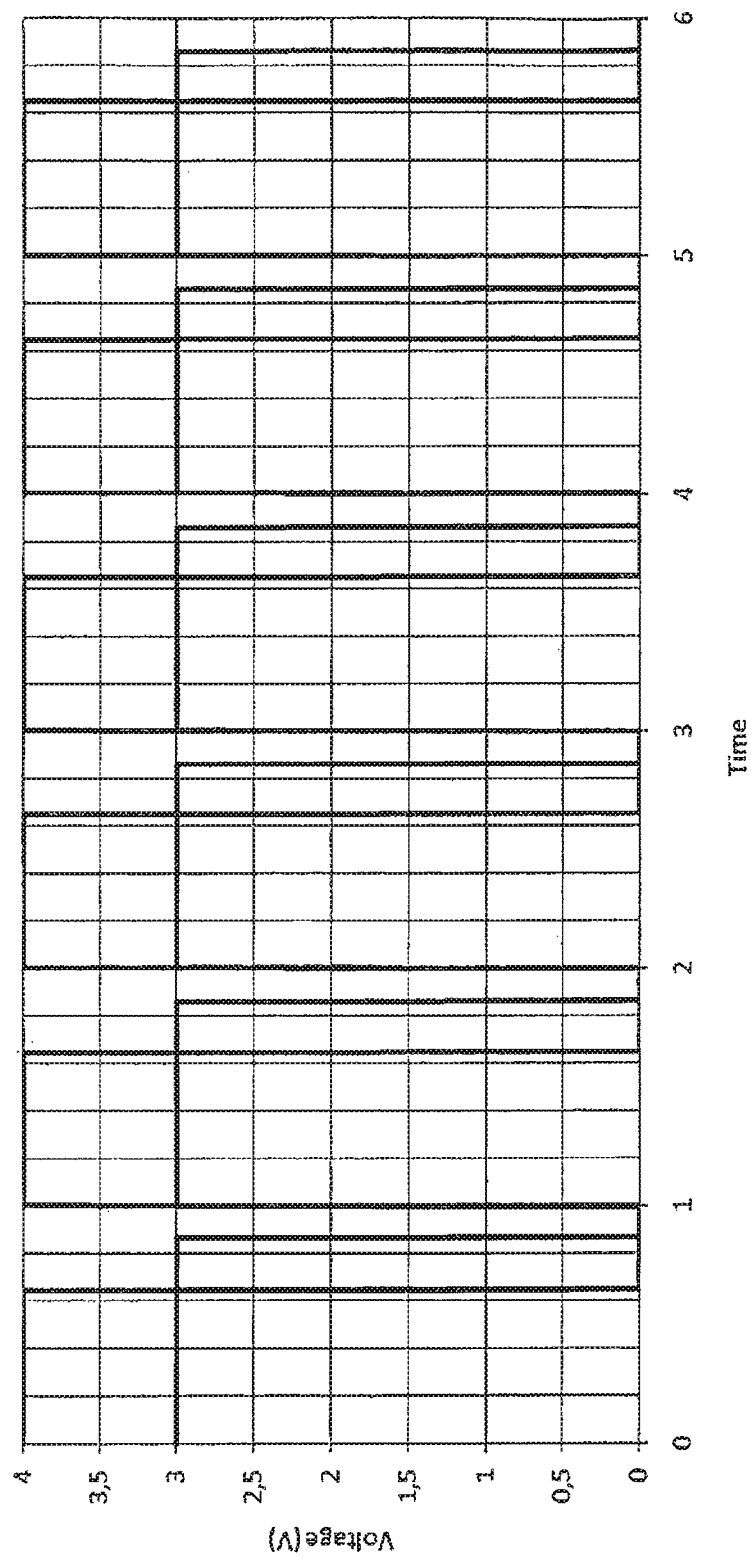

(51) Int. Cl.
*A61M 11/04* (2006.01)
*H05B 1/02* (2006.01)

(52) U.S. Cl.
CPC ............. *H05B 1/02* (2013.01); *H05B 1/0297* (2013.01); *A61M 2205/3653* (2013.01); *A61M 2205/8206* (2013.01)

(56) References Cited

U.S. PATENT DOCUMENTS

| | | | | |
|---|---|---|---|---|
| 5,954,979 | A * | 9/1999 | Counts | A24F 47/008 |
| | | | | 131/194 |
| 6,040,560 | A | 3/2000 | Fleischhauer et al. | |
| 8,550,069 | B2 * | 10/2013 | Alelov | A61M 11/005 |
| | | | | 128/202.21 |
| 8,820,330 | B2 * | 9/2014 | Bellinger | A61M 11/041 |
| | | | | 128/202.21 |
| 2008/0257367 | A1 * | 10/2008 | Paterno | A24F 47/008 |
| | | | | 131/328 |
| 2011/0265806 | A1 | 11/2011 | Alarcon et al. | |
| 2011/0304282 | A1 | 12/2011 | Li et al. | |
| 2013/0104916 | A1 | 5/2013 | Bellinger et al. | |
| 2013/0192615 | A1 | 8/2013 | Tucker et al. | |
| 2014/0251324 | A1 | 9/2014 | Xiang | |
| 2014/0261489 | A1 * | 9/2014 | Cadieux | A24F 47/008 |
| | | | | 131/328 |

FOREIGN PATENT DOCUMENTS

| | | |
|---|---|---|
| EP | 2460423 A1 | 6/2012 |
| WO | 1994006314 | 3/1994 |
| WO | 2013060781 A1 | 5/2013 |
| WO | 2014150942 A2 | 9/2014 |

OTHER PUBLICATIONS

Intellectual Property Office, Combined Search and Examination Report issued in GB Patent Application No. 1412224.6 (dated Jan. 9, 2015).

* cited by examiner

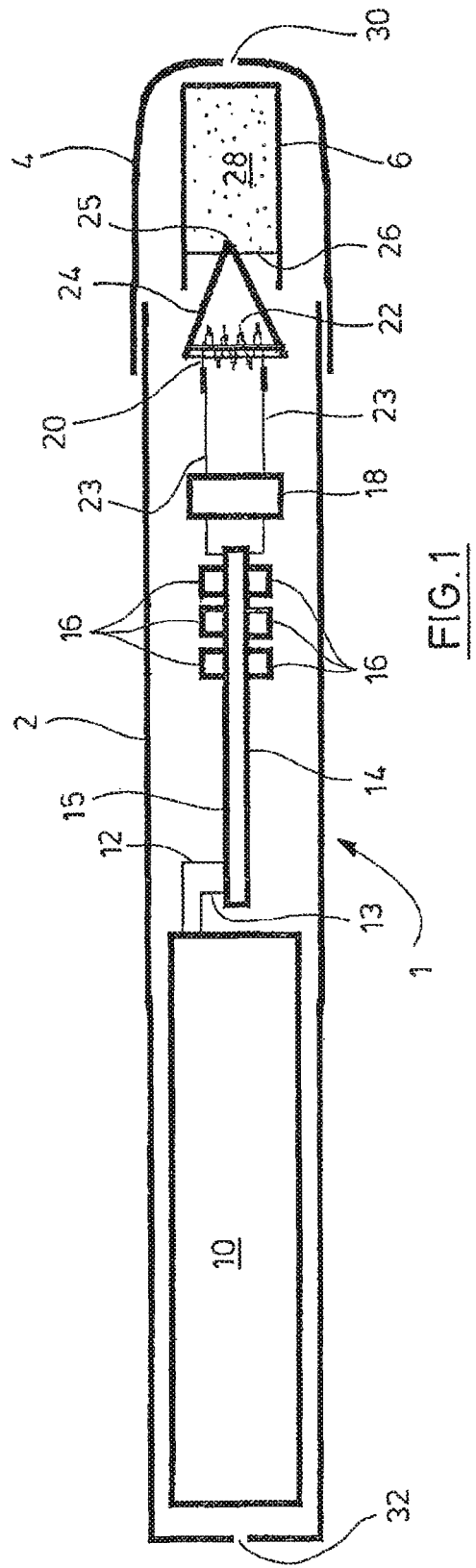
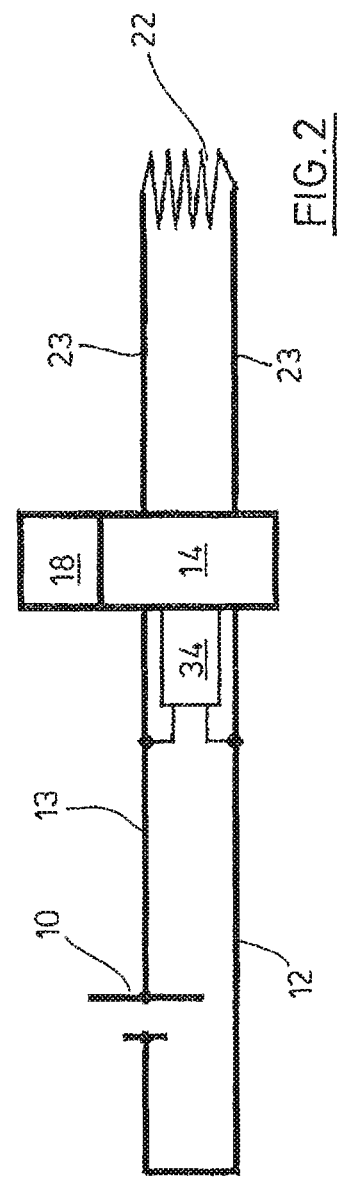

ELECTRONIC SMOKING DEVICE WITH HEATER POWER CONTROL

The invention relates to an electronic smoking device, in particular an electronic cigarette.

An electronic smoking device, e.g. designed as an electronic cigarette, generally comprises a housing accommodating an electric power source (usually a battery or a rechargeable battery), an electrically heatable atomizer including an electric heater adapted to atomize a liquid supplied from a reservoir (usually a capsule) in order to provide an aerosol exiting from the atomizer, and control electronics which control the heater of the atomizer. A puff detector indicates or signals an aerosol inhaling puff to the control electronics. Usually, the puff detector is designed as an inhaling sensor detecting a user's puff, but it can also be accomplished, e.g., as a simple push button pressed by the user while inhaling the aerosol. When a puff is indicated to the control electronics, the heater in the atomizer is powered, which causes the creation of aerosol. Here and in the following, the action of the atomizer is called "atomize" and the related product is called "aerosol", irrespective of its composition, which might include gaseous and smoke constituents.

EP 2 443 946 A1 discloses an electronic cigarette and a capsule containing a liquid to be atomized (or evaporated) in an atomizer. The capsule comprises a shell which is sealed at one end side by a puncturable membrane. To mount the capsule at the mouth-ended side of the electronic cigarette, a soft sleeve surrounding the capsule is placed on the end area of a tube accommodating the atomizer. During the mounting step, a spike provided at the end of a kind of metal, wick pierces the membrane, and the liquid of the capsule is guided by the wick to the atomizer. The aerosol generated by the atomizer passes the area of the capsule through some ducts provided at the exterior surface of the capsule to reach an end opening where it can be inhaled by the consumer.

US 2011/0304282 A1 describes a power supply section for an electronic cigarette. This section comprises an elongate housing sleeve, which accommodates a rechargeable battery, an inhaling sensor for detecting an aerosol inhaling puff of a user, and control electronics connected to the inhaling sensor and adapted to control the heater of an atomizer. At an end side of the housing sleeve, a connector provides a mechanical support to a mouth-sided section of the electronic cigarette, which comprises the atomizer and holds a capsule containing a liquid to be atomized. The connector includes electrical connections for the atomizer.

In the known electronic smoking devices, the heater of the atomizer is generally driven by the voltage provided by the battery and powered for a certain time period, usually the period during which the inhaling sensor signals the presence of a puff or for a pre-determined period. When the battery is discharged during use, its voltage drops so that the power of the heater decreases, which results in less intensive puffs. In some devices, the user can influence the heater by external settings, which might affect the aerosol emerging from the atomizer in an undesired manner, however. Generally, when the heater is not hot enough, aerosol creation is poor or stops completely. On the other hand, when the heater gets too hot, too much aerosol is created or, even worse, aerosol substances may burn or disintegrate, and the battery is discharged too quickly. It would be desirable to measure the temperature of the heater, but this would require a temperature sensor close to the heater, implying an appreciable technical effort.

U.S. Pat. No. 6,040,560 discloses a power controller for an electrical smoking system which externally heats a tobacco-containing cigarette. This controller uses a power cycle including at least two phases, each having a predetermined total energy input.

The object of the invention is to provide an electronic smoking device, in which the heater of the atomizer can be operated in a simple, reliable and reproduceable manner, largely independent of changes of the battery voltage.

This object is achieved by an electronic smoking device having the features of claim 1. Advantageous embodiments of the invention follow from the dependant claims.

The electronic smoking device according to the invention comprises a housing, which accommodates a battery as an electric power source powering an electrically heatable atomizer. The atomizer comprises an electric heater and is able to atomize a liquid supplied from a reservoir to provide an aerosol exiting from the atomizer. Moreover, the electronic smoking device comprises control electronics and a puff detector. The puff detector, for example an inhaling sensor or a manually actuatable switch (see below), indicates an aerosol inhaling puff to the control electronics. The control electronics are adapted to control the heater of the atomizer. For example, when the puff detector detects a puff and indicates or signals that to the control electronics, the heater is powered by means of the control electronics in order to create aerosol.

According to the invention, the control electronics operates, for a puff, the heater of the atomizer with a pre-determined level of electric power. That means, the electric power (i.e. electric energy per time unit) supplied to the heater is controlled in a way so that it is maintained at the pre-determined level for the actual puff. This does not exclude fluctuations of the power during the puff, provided the fluctuations are on a time scale which is short compared to the duration of the puff. In other words, the electric power by which the heater is operated is kept constant at the pre-determined level, during the puff, to a rather high degree of accuracy. Thus, the conditions during an inhaling puff are largely reproducable, even when the battery voltage drops due to consumption and discharging. Given the latent heat for aerosol production in the atomizer and the thermal losses due to radiation and convective heat transport by means of the aerosol, the pre-determined power level may correspond to a more or less well-defined temperature of the heater and the atomizer. Such a general relation between power and temperature permits a pre-selection of a suitable power level, which in practice is preferably performed experimentally.

A complete electronic smoking device according to the invention, for example an electronic cigarette, may include components in addition to the housing, the puff detector and the control electronics mentioned above. For example, the atomizer and the reservoir may be accommodated in a separate section connected to the above housing. However, per definition the term "electronic smoking device" is also used for a device just including the housing, the puff detector and the control electronics because that device is related to electronic smoking and might be marketed separately. In this sense, the battery (which is mounted in the housing, but which usually is replaceable), the atomizer and/or the reservoir may be or may be not components of the electronic smoking device.

In advantageous embodiments, the electronic smoking device according to the invention comprises a voltage sensor. The voltage sensor measures the battery voltage and is connected to the control electronics. Moreover, the control electronics is adapted to distribute the pre-determined level of electric power, for a puff, by pulse width modulation, based on the battery voltage measured by the voltage sensor.

For example, the voltage sensor detects when the battery voltage drops in the course of time. Based on that information, the control electronics is able to adjust the duty cycle of the pulse-width-modulated voltage provided to the heater terminals. Assuming that the electrical resistance of the heater is largely constant, i.e. independent of temperature (see below) and has a pre-determined value, an instantaneous voltage level at the heater terminals corresponds to a certain instantaneous current flowing through the heater (current=voltage/resistance) and thus to a certain instantaneous electrical power dissipated in the heater resistance (power=voltage×current=voltage$^2$/resistance). The voltage supplied to the heater terminals can be the battery voltage. Thus, the pre-determined level of electric power can be maintained as long as it is smaller than (battery voltage)$^2$/resistance, and the control is performed via the duty cycle of the pulse width modulation. This will be explained in more detail by means of an embodiment, see below.

If the electrical resistance of the heater is not constant, pulse width modulation may be used as well. In any case, a look-up table determining the relation between measured battery voltage and duty cycle can be established experimentally, for a pre-determined electrical power.

Due to the internal resistance of the battery, the battery voltage available at the terminals of the battery depends on the current flowing through the heater. Since the current is switched on and off in pulse width modulation, the battery voltage will change during a puff. Additionally, when no current is flowing, the battery voltage recovers as a function of time, which also depends on the charge state of the battery.

In practice, the battery voltage fluctuates during a puff, which creates the problem of selecting appropriate values for the battery voltage in order to run the pulse width modulation in a reliable manner.

In advantageous embodiments of the invention, the control electronics is adapted to receive multiple measured values of the battery voltage during a puff and to derive a representative value of the battery voltage therefrom. This representative value is taken as an appropriate value for the battery voltage, which can be used for determining the duty cycle of the pulse width modulation. In principle, the representative value of the battery voltage might be selected by an analogue technique, e.g. by filtering, which takes some average over the fluctuations.

A digital technique may be more advantageous, however. For example, the control electronics can be adapted to derive the representative value of the battery voltage as the smallest individually measured value of the battery voltage plus a constant. In other words, the battery voltage is frequently measured during a certain puff (puff n), and the results are stored. Lower measured values tend to be associated with the heater being switched on and are representative for the battery under load. On the other hand, the lowest value of the battery voltage will not be realistic because of fluctuations and short-time recovery of the battery. Therefore, a constant is added, for example a constant of 200 mV.

The representative value of the battery voltage derived in this way during puff n can be applied in the next puff (i.e. in puff n+1) as the value for the battery voltage. That means, this value is taken as a constant value for the battery voltage during puff n+1 for the purposes of determining the pulse widths to observe the pre-determined level of electric power during puff n+1. During puff n+1, the battery voltage can be frequently measured as well, as in puff n, to derive a new representative value of the battery voltage, which is to be used in puff n+2, and so on. In this way, during each puff, the battery voltage is taken as a constant, but it is considered that the battery voltage will change with increasing puff number. For the first puff (puff 1), e.g. the first puff after the battery has been freshly charged, an empirical value can be taken as the representative value of the battery voltage, e.g. the nominal voltage (highest voltage) of a lithium ion battery minus an empirical correction constant.

In other embodiments, the control electronics receives multiple measured values of the battery voltage during a puff and re-adjusts the pulse widths (duty cycle) during a puff to observe the pre-determined level of electric power. That means that the control electronics is able to react on changes of the battery voltage during a puff and to adjust the duty cycle accordingly still during this puff.

The voltage sensor can be integrated in the control electronics. It may also be provided as an independent voltage meter. A person skilled in the art knows many possibilities for accomplishing a voltage sensor for measuring the battery voltage and transmitting the result to the control electronics. For example, the battery voltage can be measured by using an ADC (analog-to-digital converter) either integrated in a microcontroller (system on chip) or provided as an independent IC (integrated circuit) that is connected through an I2C (inter-integrated circuit bus) or SPI (serial peripheral interface bus) interface to the microcontroller or system on chip.

There are several options for the kind of response initiated when a puff is indicated to the control electronics. In an advantageous embodiment, the control electronics is adapted to operate, upon indication of a puff, the heater of the atomizer with the pre-determined level of electric power as long as the puff is indicated. That means, the amount of energy delivered to the heater (and thus the amount of aerosol created) is variable and depends on the length of the puff. In another embodiment, the control electronics is adapted to operate, upon indication of a puff, the heater of the atomizer with the pre-determined level of electric power for a pre-determined period. In that case, indication of a puff just triggers a pre-determined action, i.e. the delivery of a pre-selected amount of electrical energy to the atomizer.

In advantageous embodiments of the invention, the control electronics operates the heater of the atomizer with a reduced level of electric power, when it is not operated with the pre-determined level of electric power. That means, in the intervals between the puffs, the heater is not switched off, but run at a lower temperature, which avoids that the heater cools down too much so that it can be quickly re-activated upon demand. On the other hand, the overall energy consumption is higher in this operating mode.

As already explained further above, the puff detector transmits (indicates) to the control electronics the message that the user takes an inhaling puff. To this end, a manually actuatable switch (e.g. a push button) is sufficient, which is pressed by the user during inhaling. In a more elaborate design, the puff detector comprises an inhaling sensor, e.g. a sensor detecting a vacuum or an air flow in the housing of the electronic smoking device, which is created when the user is inhaling at a mouthpiece.

In advantageous embodiments of the invention, the heater of the atomizer comprises a heating resistor, wherein the material of the heating resistor comprises a nickel-chromium alloy, a nickel-chromium alloy comprising 80% per weight nickel and 20% per weight chromium (NiCr alloy 80/20), a film polyimide, and/or an iron-chromium-aluminium alloy (FeCrAl alloy, Kanthal alloys). The temperature dependence of the electrical resistivity is relatively low for these alloys, which facilitates the control of the atomizer.

The battery can be a component of the electronic smoking device. Preferably, the battery is designed as a re-chargeable lithium ion battery protected by safety circuitry. In this case, the control electronics described so far does not monitor the charge-state of the battery in order to prevent the battery from completely discharging or from over-charging. Such safety-relevant tasks are performed by the safety circuitry, which may be designed as a part of the battery.

In the following, the invention is explained in more detail by means of examples. The drawings show in FIG. 1 a schematic longitudinal section of an embodiment of the electronic smoking device according to the invention, FIG. 2 a block diagram of the electronics of the embodiment according to FIG. 1, and FIG. 3 a graphical representation of the voltage applied to an electric heater of an atomizer of the embodiment according to FIG. 1 as a function of time (pulse width modulation).

FIG. 1 illustrates an embodiment of an electronic smoking device 1 in a schematic longitudinal section.

The electronic smoking device 1 comprises a cylinder-like housing 2 and a mouthpiece 4, which is designed as a detachable cap. Taking off the mouthpiece 4 provides access to a replaceable capsule 6, which serves as a reservoir for a liquid.

The housing 2 accommodates a battery 10. In the embodiment, the battery 10 is designed as a re-chargeable lithium ion battery and includes its own safety circuitry. The battery 10 is connected, via leads 12 and 13, to control electronics 14, which includes integrated circuits mounted on a printed circuit board 15. The printed circuit board 15 also supports a plurality of light-emitting diodes (LEDs) 16, which are assembled behind respective windows provided in the housing 2 and indicate the current status of the electronic smoking device 1.

A puff detector 18 is connected to the control electronics 14. In the embodiment, the puff detector 18 is designed as an inhaling sensor, which detects the vacuum generated inside the housing 2 when a user inhales at the mouthpiece 4.

An atomizer 20 comprises a heater 22 connected via leads 23 to the control electronics 14. The heater 22 includes a heating wire mounted at a ceramics shell (not shown in the Figures), which also supports a wick device 24 made of braided metal or sponge-like metal material. A piercing tip 25 at the distant end of the wick device 24 is able to penetrate a membrane 26 used for sealing the capsule 6 so that liquid 28 contained in the capsule 6 can be guided out of the capsule 6 and through the wick device 24 to the area of the heater 22.

At its free end, the mouthpiece 4 comprises an inhaling aperture 30. At the opposite end of the electronic smoking device 1, a charging port 32 is provided which permits re-charging of the battery 10, e.g. via a USB port.

To use the electronic smoking device 1, a consumer inserts a fresh capsule 6 so that its membrane 26 is pierced and liquid is supplied from the capsule 6 via the wick device 24 to the area of the heater 22. When the consumer inhales at the inhaling aperture 30, the puff detector 18 senses the resulting vacuum inside the housing 2 and indicates that to the control electronics 14. In response thereto, the heater 22 is powered so that its heating wire is able to atomize the liquid in its proximity in order to create an aerosol, which is inhaled by the consumer. In the embodiment, the heater remains switched on as long as the puff detector 18 senses a vacuum.

FIG. 1 is a schematic illustration of the general set-up of the electronic smoking device 1. The functional set-up of the electronic smoking device 1 is shown in FIG. 2 in a more appropriate way, by means of a block diagram of the electronics.

According to FIG. 2, the battery 10 is connected to the control electronics 14 via the leads 12 and 13. The puff detector 18 is displayed as a block connected to the control electronics 14, because its output signal is fed to the control electronics 14. The heater 22 is also connected to the control electronics 14, by means of the leads 23. In the embodiment, the heater 22 comprises a heating resistor made of wire of a nickel-chromium alloy (80% per weight nickel and 20% by weight chromium). Other materials for the heating resistor, which are well-known in the art, are conceivable as well. The above nickel chromium alloy has the advantage of a low dependency of the electrical resistivity on temperature. So far, the components shown in FIG. 2 are present in FIG. 1 as well.

Moreover, FIG. 2 displays a voltage sensor 34, which is connected between the leads 12 and 13 of the battery 10 and detects the actual battery voltage. The output of the voltage sensor 34 is supplied to the control electronics 14. In the embodiment, the voltage sensor 34 is designed as a component of the control electronics 14. The voltage sensor 34 comprises an analogue-to-digital converter (ADC) which outputs a numerical value representative for the actual battery voltage, which can be processed by a micro-processor which is part of the control electronics 14. Other embodiments of the voltage sensor 34 are conceivable as well.

During use of the electronic smoking device 1, the voltage of the battery 10 drops due to discharging. This process is monitored by the voltage sensor 34 so that the control electronics 14 is quasi continuously informed on the charge state of the battery 10. In order to operate the heater 22 of the atomizer 20, for each puff, with a pre-determined level of electric power, the control electronics 14 distributes the electric power supplied to the heater 22 by pulse width modulation, based on the battery voltage measured by the voltage sensor 34. When the battery voltage changes, the duty cycle of the pulse width modulation is adjusted so that the resulting power is maintained at the predetermined value.

In the embodiment, an appropriate value for the battery voltage in each puff is determined in the following way.

The control electronics 14 receives, via the voltage sensor 34, multiple measured values of the battery voltage during a puff, and these values are stored. A puff is typically considerably longer than a typical measurement time for the battery voltage, which in turn is considerably longer than the period of pulse width modulation. In the embodiment, the measurements of battery voltage and the period of pulse width modulation are not synchronised to each other.

At the end of the puff (called "puff n"), a representative value of the battery voltage is derived from the stored measured values. To this end, the control electronics 14 selects the smallest battery voltage value measured during this puff and adds a constant thereto. Appropriate values for the constant can be determined empirically. In the embodiment, the constant is 200 mV.

The representative value of the battery voltage derived in this way during puff n is applied in the next puff (i.e. in puff n+1) as the value for the battery voltage. That means, this value is taken as the battery voltage during puff n+1 for the purposes of determining the pulse widths (duty cycle) to keep the electric power delivered to the heater 22 during puff n+1 at the pre-determined constant level.

During puff n+1, however, the battery voltage is also frequently measured, as in puff n, to derive a new representative value of the battery voltage, which is to be used in puff n+2, and so on. In this way, during each puff, the battery voltage is assumed to be a constant, but it is taken into consideration that the battery voltage will change with increasing puff number, i.e. that it usually will decrease due to discharging of the battery.

For the first puff (puff 1), e.g. the first puff after the battery 10 has been freshly charged, an empirical value can be taken as the representative value of the battery voltage, e.g. the nominal voltage (highest voltage) of a lithium ion battery minus an empirical correction constant.

When the puff detector 18 does not sense a vacuum inside the housing 2, the heater 22 is not powered. Alternatively, during these intervals the heater 22 may be operated at a reduced or even much reduced power level in order to keep some elevated temperature at the atomizer 20, which permits a faster restart of the atomizer 20 when the next puff is detected. Such a reduced power level can also be controlled by means of pulse width modulation, by applying a different duty cycle.

In the following, a numerical example is given which explains the operation of the heater 22 by means of pulse width modulation of the voltage applied to the heater leads 23. In this example, the heater 22 is considered as an Ohmian resistor having a constant resistance of R=2.25 Ohms, neglecting any inductive or capacitive effects. The required duty cycle, as a function of the actual battery voltage (i.e. the representative value of the battery voltage described above), for achieving a constant heater power of $P_0$=3 W is determined by a simple calculation. The results can be stored as a look-up table in a memory so that a microprocessor of the control electronics 14 can select the duty cycle in response to a representative value of the battery voltage. Inductive or capacitive effects may be taking into consideration, for example, by empirical corrections of the duty cycle values in the look-up table.

FIG. 3 schematically illustrates the voltage pulses supplied to the heater 22 as a function of time. The time unit is relative, i.e. related to the period of one complete pulse. In the embodiment, this period is about 4 ms, which is very short compared to the typical duration of one puff (several seconds). During each pulse, either the actual battery voltage or zero voltage is supplied, and the respective duty cycle is taken from the look-up table. FIG. 3 shows the pulses for two different battery voltages, i.e. 3 V and 4 V.

Using Ohm's law (U=R·I, with battery voltage U, heater resistance R and heater current I), the power P dissipated in the heater 22 during the switched-on state of one pulse is $P=U \cdot I=U^2/R$. This state lasts for a fraction c of one pulse period. During the fraction (1−c), the voltage is switched off. Thus, c can be calculated by $c \cdot P=P_0$ or $c=P_0 \cdot R/U^2$. The duty cycle of the pulse is determined by c.

The following table provides c as a function of the battery voltage U. It is assumed that U drops from an initial value of 4.2 V to 2.9 V. When the battery voltage gets too low, the battery 10 is disabled by its own safety circuitry.

| Battery voltage U [V] | c |
| --- | --- |
| 2.9 | 0.803 |
| 3.0 | 0.750 |
| 3.1 | 0.702 |
| 3.2 | 0.659 |
| 3.3 | 0.620 |
| 3.4 | 0.584 |
| 3.5 | 0.551 |
| 3.6 | 0.521 |
| 3.7 | 0.493 |
| 3.8 | 0.467 |
| 3.9 | 0.444 |
| 4.0 | 0.422 |
| 4.1 | 0.402 |
| 4.2 | 0.383 |

In practice, the look-up table can be calculated and stored in finer steps.

The invention claimed is:

1. An electronic smoking device, comprising:
a housing adapted to accommodate a battery powering an electric heater of an atomizer adapted to atomize a liquid supplied from a reservoir to provide an aerosol exiting from the atomizer;
control electronics adapted to control the electric heater of the atomizer;
a puff detector adapted to indicate an aerosol inhaling puff to the control electronics;
the control electronics is adapted configured to operate, for a puff, the electric heater of the atomizer with a pre-determined level of electric power; and
a voltage sensor measuring a voltage of the battery, the voltage sensor connected to the control electronics, and the control electronics configured to distribute the pre-determined level of electric power, for a puff, by pulse width modulation, based on the measured battery voltage.

2. The electronic smoking device of claim 1 with the control electronics adapted to receive multiple measured values of the battery voltage during a puff and to re-adjust the pulse widths during the puff to observe the predetermined level of electric power.

3. The electronic smoking device of claim 1 wherein the control electronics is adapted to determine a required pulse width modulation by using a pre-determined, constant value of the electrical resistance of the electric heater.

4. The electronic smoking device of claim 1 wherein the voltage sensor is integrated in the control electronics.

5. The electronic smoking device of claim 1 wherein the control electronics is adapted to operate, upon indication of a puff, the electric heater of the atomizer with the pre-determined level of electric power for a pre-determined period.

6. The electronic smoking device of claim 1 wherein the control electronics is adapted to operate, upon indication of a puff, the electric heater of the atomizer with the pre-determined level of electric power as long as the puff is indicated.

7. The electronic smoking device of claim 1 wherein the control electronics is adapted to operate the electric heater of the atomizer with a reduced level of electric power, when it is not operated with the pre-determined level of electric power.

8. The electronic smoking device of claim 1 wherein the puff detector comprises a manually actuatable switch.

9. The electronic smoking device of claim 1 wherein the puff detector comprises an inhaling sensor.

10. The electronic smoking device of claim 1 wherein the atomizer is a component of the electronic smoking device and the electric heater comprises a heating resistor, wherein the material of the heating resistor comprises at least one of the following materials: a nickel-chromium alloy, a nickel-chromium alloy comprising 80% per weight nickel and 20% per weight chromium, a film polyimide, an iron-chromium-aluminum alloy.

11. The electronic smoking device of claim 1 wherein the battery is a component of the electronic smoking device and the battery is a re-chargeable lithium ion battery protected by safety circuitry.

12. The electronic smoking device of claim 1 with the control electronics adapted to receive multiple measured values of the battery voltage during a puff and to derive a representative value of the battery voltage from the multiple measured values of the battery voltage.

13. The electronic smoking device of claim 12 with the control electronics adapted to apply the representative value of the battery voltage derived during the puff as a constant value for the battery voltage when determining the pulse widths during a subsequent puff to observe the pre-determined level of electric power.

14. The electronic smoking device of claim 12 with the control electronics adapted to derive the representative value of the battery voltage as the smallest individually measured value of the battery voltage plus a constant.

15. The electronic smoking device of claim 14 wherein the constant is 200 mV.

16. An electronic smoking device, comprising:
a battery, control electronics and an atomizer in a housing, the atomizer including an electric heater for atomizing a liquid;
a puff detector electrically connected to the control electronics;
a battery voltage sensor electrically connected to the battery and to the control electronics;
the control electronics configured to operate the electric heater with a pre-determined level of electric power during a puff detected by the puff detector, based on a battery voltage measured by the battery voltage sensor, wherein the electric power supplied to the heater is maintained at the predetermined level over the duration of the puff.

17. The electronic smoking device of claim 16 with the control electronics configured to distribute the pre-determined level of electric power, for a puff, by pulse width modulation.

18. A method for controlling an electronic smoking device having a battery powering an electric heater of an atomizer adapted to atomize a liquid supplied from a reservoir to provide an aerosol exiting from the atomizer, with the battery and the atomizer in a housing and the control electronics adapted to control the electric heater of the atomizer, comprising:
detecting a puff using a puff detector and providing an indication of a detected puff to the control electronics;
measuring multiple values of a voltage of the battery during the puff using a voltage sensor connected to the battery and to the control electronics;
deriving a representative value of the battery voltage from the multiple measured values of the battery voltage; and
distributing a pre-determined level of electric power, during the puff, to the electric heater based on the representative value, wherein the electric power supplied to the heater is maintained at the predetermined level over the duration of the puff.

19. The method of claim 18 with the control electronics adapted to derive the representative value of the battery voltage as the smallest individually measured value of the battery voltage plus a constant, and with the control electronics distributing the pre-determined level of electric power by pulse width modulation.

* * * * *